United States Patent [19]

Wong

[11] Patent Number: 4,555,515
[45] Date of Patent: Nov. 26, 1985

[54] PYRIDYLPROPYL CARBAMATES AS INSECT REPELLENTS

[75] Inventor: Rayman Y. Wong, Richmond, Calif.

[73] Assignee: Stauffer Chemical Co., Westport, Conn.

[21] Appl. No.: 705,171

[22] Filed: Feb. 25, 1985

[51] Int. Cl.[4] .......................................... C07D 213/53
[52] U.S. Cl. .................................... 514/357; 546/335
[58] Field of Search ......................... 546/335; 514/347

[56] References Cited

U.S. PATENT DOCUMENTS

| | | | |
|---|---|---|---|
| 3,284,461 | 11/1966 | Wilbert | 546/335 |
| 4,348,400 | 9/1982 | Wong | 546/342 |
| 4,407,807 | 5/1983 | Wong | 424/263 |
| 4,412,997 | 11/1983 | Wong | 424/263 |
| 4,457,934 | 1/1984 | Wong | 546/342 |

FOREIGN PATENT DOCUMENTS

| | | | |
|---|---|---|---|
| 42-25666 | 7/1967 | Japan | 546/335 |
| 1132988 | 11/1968 | United Kingdom | 546/335 |

*Primary Examiner*—Henry R. Jiles
*Assistant Examiner*—P. Ann Bucci
*Attorney, Agent, or Firm*—Joel G. Ackerman

[57] ABSTRACT

Compounds having the formula

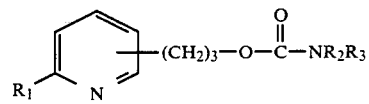

in which $R_1$ is hydrogen or $C_1$–$C_4$ alkyl and $R_2$ and $R_3$ are $C_1$–$C_4$ alkyl are insect repellents.

2 Claims, No Drawings

PYRIDYLPROPYL CARBAMATES AS INSECT REPELLENTS

This invention relates to compounds having the formula

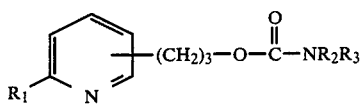

in which $R_1$ is hydrogen or $C_1$-$C_4$ alkyl and $R_2$ and $R_3$ are $C_1$-$C_4$ alkyl. Preferably $R_2$ is hydrogen or methyl. The side chain may be attached to the pyridine ring at the 2-, 3- or 4-position.

As will be shown from the data which follows, these compounds have been found to have utility in repelling insects, particularly repelling flying insects, and most particularly houseflies, from lighting and/or feeding.

The compounds of this type can be prepared by reaction of an appropriate pyridyl propanol with a carbamyl halide (preferably chloride) according to the reaction (X stands for halogen):

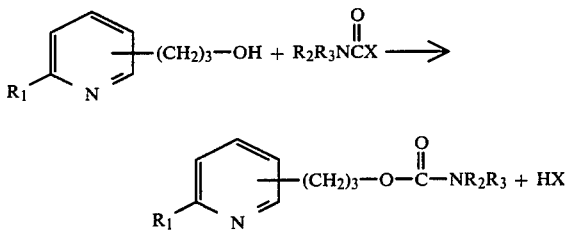

The pyridyl propanols in which R is $C_1$-$C_4$ alkyl, if not commercially available, can be synthesized for example by the method of Umezawa et al., Japanese Patent Application No. 74/13180.

The reaction to produce the desired compounds is generally conducted at temperatures of from about 0° C. to about 25° C. in the presence of a solvent such as dimethylformamide, or other suitable inert solvent and sodium hydride. The reaction is preferably carried out in two steps—first the pyridyl propanol is reacted with sodium hydride to form a sodium salt; then the salt is reacted with the carbamyl halide. The product is recovered by conventional extraction, washing, filtration, and other purification steps as may be necessary.

The preparation of these compounds is illustrated by the following example.

EXAMPLE 1

Preparation of N,N-Dimethyl-3(3-pyridyl)propyl carbamate (Compound No. 1 herein)

In a flask equipped with a stirrer, there was placed 1.2 grams (g) of sodium hydride in oil. The hydride was washed with tetrahydrofuran, dried under vacuum, and an argon blanket established. Then, 50 milliliters (ml) dimethylformamide was added, followed by 5.0 g (0.036 mole) 3-(3-pyridyl)-1-propanol, plus some tetrahydrofuran. The reaction mixture was then stirred for about 40 hours at room temperature.

The sodium salt solution was cooled to 0° C.; then 4.3 ml (5.0 g, 0.046 mole) dimethylcarbamyl chloride was added, with the temperature maintained at about 15° C. maximum. When addition was complete the mixture was warmed to room temperature and stirred for 66 hours, with addition of dimethylformamide to dilute it when it became thick. The product was quenched by addition of 25 ml water, and extracted with methylene chloride. The organic layer was separated, filtered and dried. The product was obtained by evaporation and was purified by liquid chromatography to produce 2.5 g (33% of theoretical yield) of the desired product, a clear yellow oil, $n_D^{30}$ 1.5040. Structure was confirmed by nuclear magnetic resonance, infrared and mass spectroscopy.

The following Table I shows representative compounds of this invention which were prepared by the above process, and whose structure was similarly confirmed by analyses.

TABLE I

| Compound Number | $R_1$ | $R_2$ | $R_3$ | Position on Pyridine Ring | $n_D^{30}$ |
|---|---|---|---|---|---|
| 1 | H | $CH_3$ | $CH_3$ | 3- | 1.5040 |
| 2 | $CH_3$ | $CH_3$ | $CH_3$ | 2- | 1.4976 |

Insect Repellency Tests

The compounds described in Table I above were tested for insect repellency by the following procedures:

Houseflies

The insect utilized for this test was the housefly, *Musca domestica* (L.). One hundred houseflies of mixed sexes were placed in test cages. In each cage was placed a sugar cube saturated with 1.0 ml of acetone containing 1% by weight of the test compound. The cube was dried and weighed before being placed in the cage. Each cage also contained a water-saturated cotton plug to provide moisture. The test cages were placed on a turntable and rotated at 1.5 revolutions per minute to keep the flies randomly distributed inside the cage. After 48 hours the flies in each cage were anesthetized with carbon dioxide. The sugar cubes were removed and reweighed and the percentage weight loss (due to consumption by the flies) recorded. A repellency ratio, calculated as the percent weight loss of the treated sugar cube divided by the percent weight loss of a control sugar cube treated only with acetone and no test compound, was calculated. The lower the repellency ratio, the greater the repellency of the test compound. The repellency ratios of the test compound at different concentrations are shown in the following Table II.

Yellow Fever Mosquito

The insect utilized for these tests was the yellow fever mosquito, *Aedes aegypti*.

Pupae were placed in separate standard fly cages and allowed to emerge into adults. The adults were supplied with a sugar-water solution. Tests were performed at least 3 days after the adults emerged.

Test compounds were weighed and dissolved in acetone. One milliliter (ml) of the test solution was pipetted onto a 9×9 cm swatch of cotton stocking. The swatches were then allowed to dry for 1 hour.

A square opening 6×6 cm was made in an upper corner of one side of each cage. A large, hard cardboard disk was placed over the opening so that it could be rotated to either cover or expose the opening as desired. One-half of the disc was left intact. In the remaining half, several 6×6 cm square openings were cut. When the intact half of this disc was located over the opening in the cage, this opening was effectively sealed.

Swatches of treated stocking were placed over the square holes in the disc and held in place by metal frames attached to magnetic tape.

To initiate the test the disc was rotated so that a treated swatch became located over the opening in the cage. The palm of the tester's hand was placed over a cardboard ring, 8 cm in diameter and 1 cm thick. The ring acted as a spacer and protected the hand from bites which could otherwise be inflicted by the insects. A breath of air was exhaled through tubing into the opening, so that insects could be attracted to the swatch by the warm, moist air and the tester's hand. The number of insects landing on the swatch was observed, and the number probing, recorded during a 1-minute exposure. Repellency was considered to occur when 5 or fewer insects probed the swatch during the exposure.

The compounds were tested at the rate of 0.1 mg/cm² of swatch downwards. Repellency is considered to occur when fewer than ten insects per minute are observed probing. The results of these tests are contained in Table II.

TABLE II

| Compound Number | HF Repellency Ratio | YFM, Number of Insects Probing/min. |
|---|---|---|
| 1 | 0.02 | 4 |
| 2 | 0.54 | 0 |

Compound 1 was also tested for repellent activity against the hornfly, *Haematobia irritans*, and both compounds were tested for repellent activity against the stable fly, *Stomoxys calcitrans*, but no such activity was demonstrated at 0.1 mg/cm² of swatch.

The novel compounds of this invention may be used as an insect repellent in either diluted or undiluted form. When used in a diluted form, compositions may contain relatively high or relatively low concentrations of the active compound. For example, the active compound can be incorporated into relatively high concentration compositions such as wet sprays or solutions in alcohol or other suitable solvents. Such compositions may contain, in addition to the active compound, adjuvants such as emulsifying agents, surface-active agents, anti-oxidants and propellants which may be normally found in insect repellent preparations. The active compound of this invention may be employed as the sole active component of such compositions or may be used in admixture with other compounds having a similar or different utility. For example, the compound may be incorporated into creams, lotions, powders, suntan oil, insecticides and other preparations which may contain pesticidal or other useful substances, as well as into compositions of various types used for treating fabrics or articles of clothing to render them insect repellent. In general, compositions for repellent use may contain from 0.1 up to 95 weight %, preferably from 1 to about 40 weight %, of the novel compound. High concentration formulations, containing up to 95% of the compound, could also be utilized for low-volume spraying from the air.

Examples of typical formulations employing the compound of this invention are for instance,

| Component | Weight % |
|---|---|
| Example 1: Emulsifiable Concentrate | |
| Compound 1 | 53.6 |
| Aromatic Hydrocarbon Solvent | 36.4 |
| Emulsifier | 10.0 |
| Total | 100.0 |
| Example 2: Lotion | |
| Compound 2 | 10.7 |
| Lanolin | 4.8 |
| Mineral Oil | 8.0 |
| Trihydroxyethylamine stearate | 1.8 |
| Glycosterin | 0.8 |
| Glycerine | 4.6 |
| Sodium Benzoate | 1.0 |
| Water | 68.3 |
| Total | 100.0 |
| Example 3: Alcohol Solution | |
| Compound 1 | 53.6 |
| Isopropanol | 46.4 |
| Total | 100.0 |
| Example 4: Alcohol Solution | |
| Compound 2 | 80.0 |
| Ethanol | 20.0 |
| Total | 100.0 |
| Example 5: Wettable Powder | |
| Compound 1 | 26.9 |
| Hydrated Calcium Silicate | 62.1 |
| Sodium Lignosulfonate | 5.0 |
| Orzan A (mixture of ammonium lignosulfonate and wood sugars) | 5.0 |
| Wetting Agent | 1.0 |
| Total | 100.0 |

What is claimed is:

1. A method for repelling insects comprising applying to a locus to be protected from insects an amount of a compound having the formula

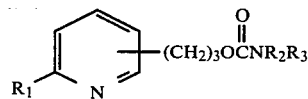

in which $R_1$ is hydrogen or $C_1$–$C_4$ alkyl and $R_2$ and $R_3$ are $C_1$–$C_4$ alkyl, effective to repel insects from said locus.

2. A method according to claim 1 in which the insect is the housefly.

* * * * *